United States Patent

Bertram et al.

[11] 4,110,354
[45] Aug. 29, 1978

[54] WATER-SOLUBLE EPOXY RESINS AND PROCESS FOR THEIR PREPARATION

[75] Inventors: James L. Bertram, Lake Jackson; Pong Su Shih, College Station, both of Tex.

[73] Assignee: The Dow Chemical Company, Midland, Mich.

[21] Appl. No.: 401,915

[22] Filed: Sep. 28, 1973

Related U.S. Application Data

[63] Continuation-in-part of Ser. No. 67,234, Aug. 26, 1970, abandoned, which is a continuation-in-part of Ser. No. 852,061, Aug. 21, 1969, abandoned, which is a continuation-in-part of Ser. No. 782,611, Dec. 10, 1968, abandoned.

[51] Int. Cl.² ............... C07D 301/28; C07D 303/24
[52] U.S. Cl. ........................ 260/348.14; 260/348.64
[58] Field of Search ............ 260/348.6, 348.14, 348.64

[56] References Cited

U.S. PATENT DOCUMENTS

| | | | |
|---|---|---|---|
| 2,581,464 | 1/1952 | Zech | 260/348 |
| 3,033,803 | 5/1962 | Price et al. | 260/2 |
| 3,298,981 | 1/1967 | Fry et al. | 260/18 |
| 3,351,574 | 11/1967 | Hicks et al. | 260/18 |
| 3,466,305 | 9/1969 | Davis et al. | 260/348 |

*Primary Examiner*—Norma S. Milestone
*Attorney, Agent, or Firm*—James G. Carter

[57] ABSTRACT

This invention is concerned with water-soluble epoxy resins represented by the general formula

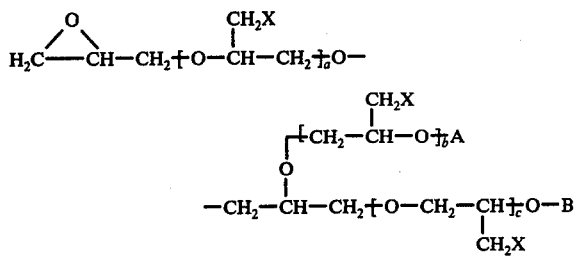

wherein A and B are independently selected from the group consisting of hydrogen and the

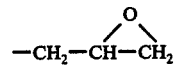

radical; X is a halogen having an atomic number from 17 to 53 inclusive and $a$, $b$ and $c$ are integers the sum of which equals a number from 0 to 3. These water-soluble glycidyl ethers of glycerine are prepared by reacting glycerine with an epoxyalkyl halide in the presence of a Lewis Acid catalyst, subsequently at least partially dehydrohalogenating the resulting product, and finally recovering the water-soluble glycidyl ether product. Both the condensation reaction and the dehydrohalogenation reaction are carried out in the presence of an organic solvent. The products of this invention are polymerizable and useful in the same way as other glycidyl ethers but additionally may be used in aqueous formulations for coatings, adhesives and the like.

2 Claims, 2 Drawing Figures

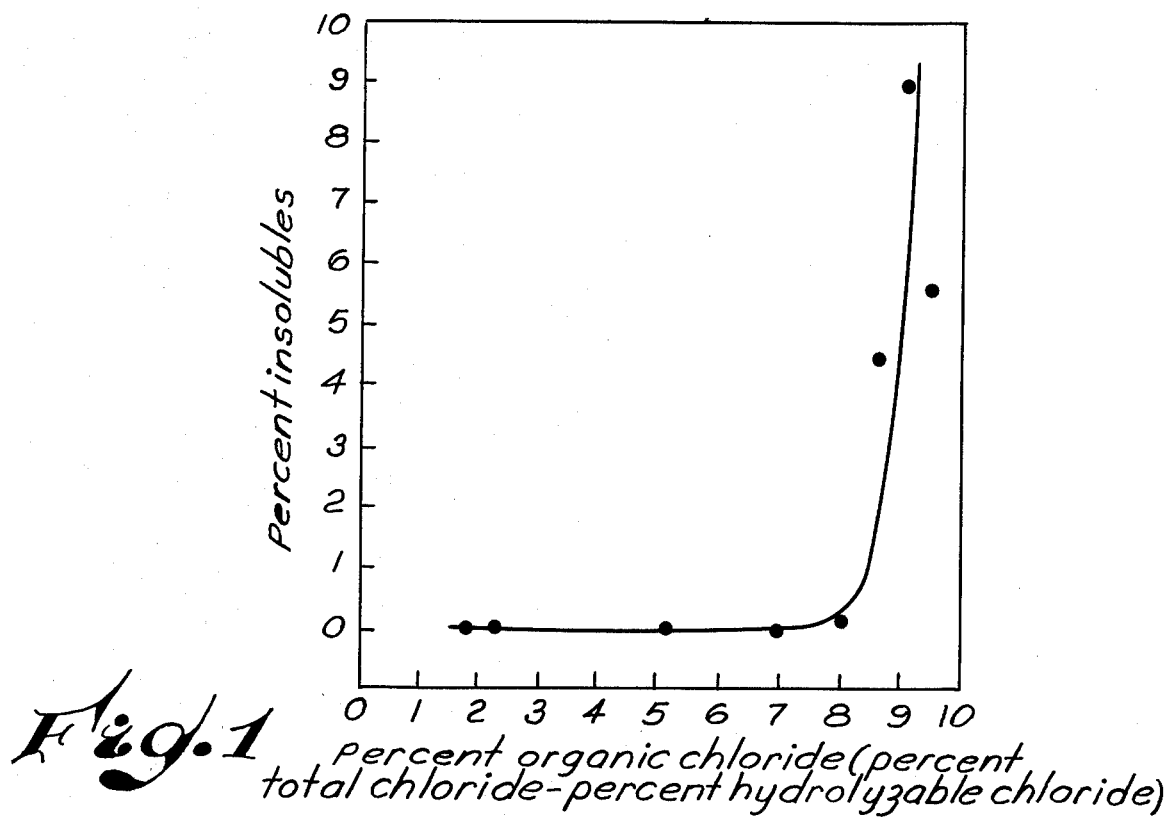
Fig. 1 percent organic chloride (percent total chloride — percent hydrolyzable chloride)
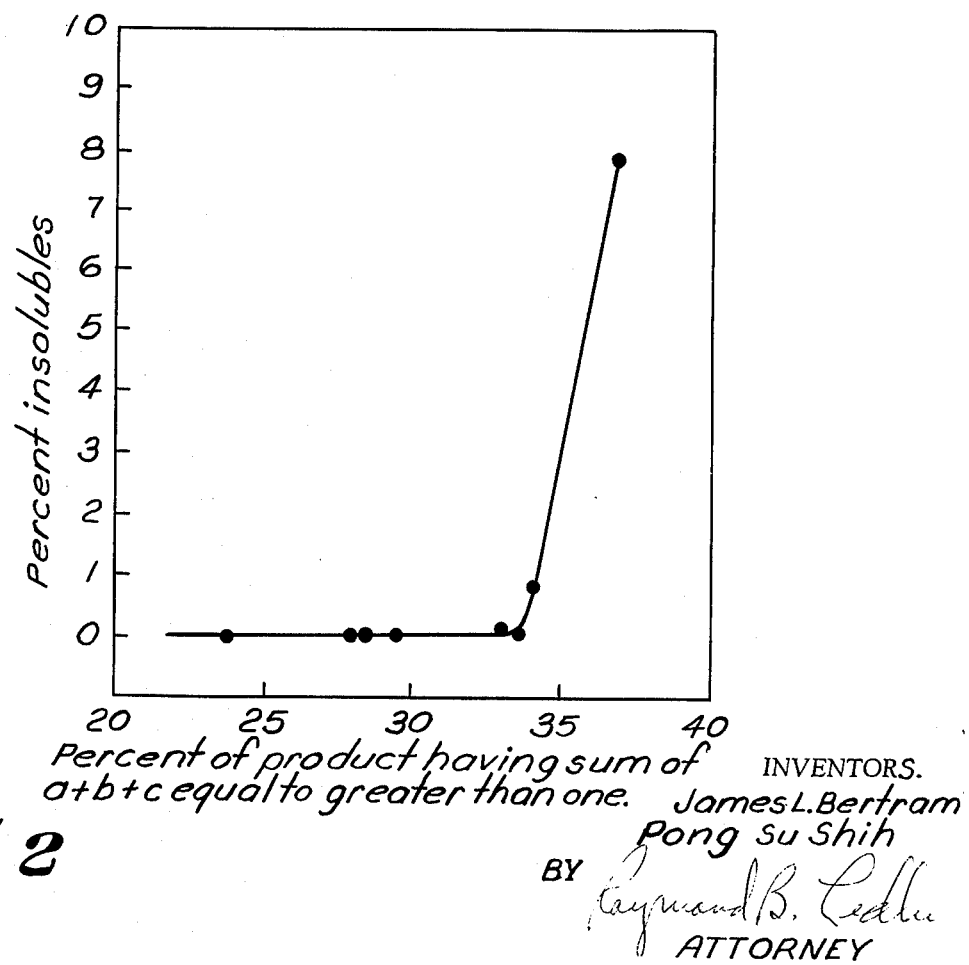
Fig. 2 Percent of product having sum of a+b+c equal to greater than one.
INVENTORS.
James L. Bertram
Pong Su Shih
BY
Raymond B. Ledlie
ATTORNEY

WATER-SOLUBLE EPOXY RESINS AND PROCESS FOR THEIR PREPARATION

This application is a continuation-in-part of our co-pending application Ser. No. 67,234, filed Aug. 26, 1970 which is a continuation-in-part of application Ser. No. 852,061, filed Aug. 21, 1969, which is a continuation-in-part of application Ser. No. 782,611, filed Dec. 10, 1968, all now abandoned.

This invention relates to novel epoxy resins which are water-soluble glycidyl ethers of glycerine and to a process for the production of such water-soluble glycidyl ethrs. More particularly, this invention relates to a novel method for conducting the reaction of glycerine with an epoxyalkyll halide to produce chlorohydrin ether which is then dehydrohalogenated to produce a glycidyl ether of glycerine which is highly water soluble.

The reaction of epoxyalkyl halides, such as epichlorohydrin, with a polyhydric alcohol in the presence of catalysts such as $H_2SO_4$ or $BF_3$, is well known in the art. It is likewise well known to dehydrohalogenate the resulting chlorohydrin ether with a base to produce a glycidyl ether. Such reactions, however, are normally conducted in the absence of any solvent other than an excess of one of the reactants and the process produces glycidyl ethers which are substantially insoluble in water.

It is an object of this invention to produce specific glycidyl ethers of glycerine with are soluble in water. A further object is to provide to the art a method for preparing such water-soluble glycidyl ethers of glycerine. These and other objects and advantages of the present invention will become apparent from a reading of the following detailed specification.

FIG. 1 is a graphical representation of the portion of the data of Example 1 showing percent organic chloride plotted versus percent insolubles.

FIG. 2 is a graphical representation of the portion of data of Example 2 showing percent solubles versus percent of product having the sum of $a$, $b$ and $c$ in the product formula equal a number greater than 1.

It has now been discovered that water-soluble glycidyl ethers of glycerine are prepared by reacting an epoxyalkyl halide with glycerine in a solvent and employing a Lewis Acid as a catalyst for such condensation reaction. The resulting chlorohydrin ether is then at least partially dehydrohalogenated with a base or alkaline-acting material in the presence of a solvent to produce the desired water-soluble glycidyl ethers of glycerine. Such glycidyl ethers may then be separated from the salt by filtration or centrifugation and separated from the solvent and water by distillation.

The water-soluble glycidyl ethers of glycerine produced by the process of this invention are represented by the formula

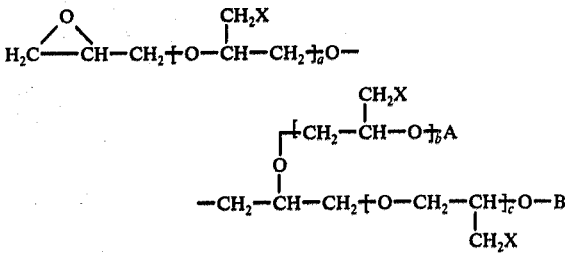

wherein A and B are independently selected from the groups consisting of hydrogen and the

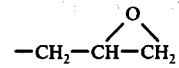

radical, X is a halogen having an atomic number from 17 to 53 inclusive and $a$, $b$ and $c$ are integers the sum of which equals a number from 0 to 3. It is understood that such product is a mixture of various possible species contemplated by the formula rather than being a pure compound.

The term "epoxyalkyl halide" as used herein, refers to a compound comprising an alkane chain or cycloalkane ring having disposed thereon a vicinal epoxy group (oxirane group) and a halogen atom attached to a chain carbon atom which is not attached to the oxygen atom. Preferred compounds are those wherein the halogen atom is attached to a chain carbon atom which is directly attached to a carbon atom of an epoxy ring, the vic-epoxy ring thus being in the alpha, beta-position relative to the halogen. These compounds have the structure

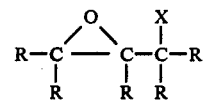

where X is a halogen atom and each R is selected from the group consisting of the hydrogen atom and alkyl groups of up to 4 carbon atoms. Representative compounds include 1-chloro-2,3-epoxypropane (epichlorohydrin; 1-bromo-2,3-epoxypropane (epibromohydrin): 1-iodo-2,3-epoxypropane (epiodohydrin); 1-chloro-2,3-epoxybutane; 1-iodo-2,3-epoxyhexane; 3-chloro-4,5-epoxyoctane; 1-chloro-2,3-epoxycyclohexane; 1-bromo-2,3-epoxy-3-methylbutane; 2-chloro-2-methyl-3,4-epoxypentane; and the like, preferably having from 3 to 8 carbon atoms per molecule. The most preferred compounds of this class, which combine a terminal halogen atom with a terminal epoxy group, are the epihalohydrins, e.g. epichlorohydrin and epibromohydrin. Because of the preponderant commercial importance of epichlorohydrin, relative to other epoxy-alkyl halides, the following description of the invention will be made largely in terms of that compound.

As used herein, the term "water-soluble" refers to glycidyl ethers of glycerine containing less than 2% by volume of insolubles as determined by the following method: 10 gm of resin (9 ml.) is admixed with water to form a total volume of 100 ml. The mixture is then shaken until no more resin is apparently going into soluton. This aqueous mixture or solution is then centrifuged to remove any material which is not in solution. The volume of such undissolved material divided by the original 9 ml. sample volume × 100 provides the percent insolubles contained in the product.

Suitable catalysts for the condensation reaction between the epoxyalkyl halide and glycerine include substantially any Lewis Acid but boron trifluoride (as the etherate), aqueous hydrofluoric acid and stannic chloride have been found to be particularly effective and are therefore usually preferred. Such catalysts are preferably employed in a proportion of about 0.01 equivalents of catalyst per glycerine hydroxy group.

It is necessary for the purposes of this invention to react the epoxyalkyl halide with glycerine in the presence of a non-aqueous solvent in which the glycerine is at least partially soluble and in which the resulting chlorohydrin ether reaction product is sufficiently soluble to form a single phase. Suitable solvents for this reaction step include ethylene dichloride (EDC), dioxane, tetrahydrofuran, ethyl ether, 2-chloroethyl ether, chloroform, methylene chloride and the like. It is usually desirable to employ the reactants in a solvent solution containing at least about 20 weight percent solvent based on the glycerine employed with at least 50 weight percent being usually preferred. If less than 20 weight percent solvent is employed, undesirable amounts of water-insoluble material are formed as the product of this process. The upper proportion of solvent to be employed is limited only by handling and economics considerations but no particular advantage is gained by employing over 90 weight percent solvent. When $SnCl_4$ or HF rather than $BF_3$ or other Lewis Acid are employed as the catalyst for this condensation step, less than 20 weight percent solvent may be employed and in some instances no solvent is required in order to achieve a water-soluble product. Even with this catalyst, however, a solvent concentration of 50 weight percent or above is preferred.

Mole ratios of epoxyalkyl halide to glycerine of from about 2:1 to about 2.6:1 are generally necessary to provide a water-soluble product which is curable into a resin having desirable physical properties. When $SnCl_4$ or HF is employed as catalysts, the mole ratio can be extended up to about 3.0:1.

A mole ratio of substantially less than 2:1 tends to produce very low molecular weight products having a relatively high proportion of monofunctional constituents, whereas a mole ratio of substantially above 2.6:1 or 3.0:1 when the catalyst is $SnCl_4$ or HF produces relatively high molecular weight products having an undesirably high proportion of molecular species wherein the sum of $a$, $b$ and $c$, as defined above, are greater than 1 and which lack the desired water-solubility. Likewise, mole ratios substantially above 2.6:1 produce products having greater than about 8 percent organic chloride and which are therefore not sufficiently water-soluble. Therefore, the water-soluble epoxy resins of the present invention have an organic chloride content of from about 1.5 to about 8.

A reaction temperature of between about 0° C and the boiling point or reflux temperature of the solvent is employed in this reaction step but a temperature between about 40° C and about 90° C is usually preferred.

Alkaline-acting materials are employed to dehydrohalogenate the chlorohydrin ether to produce the desired glycidyl ethers of glycerine. Suitable alkaline-acting materials include, for example, sodium hydroxide, potassium hydroxide, sodium and potassium carbonates and the corresponding bicarbonates, the hydroxides of magnesium, zinc, lead, iron, aluminum and the like as well as aluminates, silicates and zincates of alkali metals. Due to its availability and price sodium hydroxide is usually preferred and is most advantageously employed in a proportion of from about 70 to about 95 mole percent of the epichlorohydrin added. Amounts of NaOH less than about 70 percent produce a product having a high hydrolyzable chloride content and therefore a product having an undesirably lower epoxide content. Amounts of NaOH greater than 95% of theoretical produce higher molecular weight resins by crosslinking and such resins have insufficient water solubility. It has been found that glycidyl ethers of glycerine having a percent organic chloride of greater than about 8 wt. percent and those containing greater than about 35 wt. percent of materials having a sum of $a$, $b$ and $c$ (as above defined) which is greater than 1 are not sufficiently water soluble.

It is necessary for the process of this invention to conduct the dehydrohalogenation reaction in the presence of an organic solvent which will maintain at least the glycidyl ether of glycerine in solution. Suitable solvents for this step of the reaction include toluene, xylene, ethylene dichloride, methylene chloride, chloroform, and the like. It is particularly advantageous to conduct the dehydrohalogenation at a temperature below about 110° C and to employ a solvent which will azeotrope with water to form an azeotrope containing relatively high concentrations of water. Under reduced pressure, solvents such as toluene and xylene are effective and for atmospheric pressure distillation ethylene dichloride is particularly effective. While one solvent may be employed in the condensation step, removed and a second solvent employed in the dehydrohalogenation step, it is usually desirable to employ the same solvent in both such steps.

It is important to maintain a solvent concentration in the dehydrohalogenation step of at least about 50 weight percent, preferably between about 70 weight percent and 95 weight percent, based on the initial weight of glycerine plus the total quantity of solvent to be employed in the dehydrohalogenation reaction. For example, if 80 parts of glycerine and 20 parts of solvent are employed in the coupling reaction, the addition of 167 parts of additional solvent to the reaction mixture prior to the dehydrohalogenation reaction provides a solvent concentration at the preferred 70% level based upon the weight of glycerine initially employed plus the total weight of solvent employed in the dehydrohalogenation reaction. At solvent concentrations below about 50 percent relatively high percentages of water-insoluble high molecular weight resins are formed and gelling of the resin tends to occur. To a lesser degree such problems persist between 50 and 70 percent solvent with some resin solvent systems. Above about 95 weight percent solvent, a water-soluble resin is produced but such high volumes of solvent make recovery of the resin unduly complicated and expensive.

In one preferred embodiment of the invention, a mixture of glycerine and 0.03 mole of $BF_3$ etherate per mole of glycerine are slurried in ethylene dichloride to form a solution containing 80 weight percent ethylene dichloride based on the glycerine present. The solution is heated to 55°–60° C. and 2.5 moles of epichlorohydrin are added per mole of glycerine at a rate sufficient to maintain the temperature within the 55°–60° C. range. After the addition of epichlorohydrin, it is desirable to digest the reactant mixture for a period of time e.g. 30 minutes. After digestion, the solution is heated to a temperature of 84°–86° C. (reflux temperature) and from 0.7 to 0.95 equivalents of 50 percent NaOH per equivalent of epichlorohydrin is added to the solution. As the NaOH is added, a water-EDC azeotrope distills from the reactor. The water is continuously separated therefrom and the EDC returned to the reaction zone until no more water is collected. The reaction mixture is then cooled, the salt is removed by filtration or centrifugation and the resin product is recovered by flashing off the EDC solvent. Alternatively, the salt may be removed continuously during the dehydrohalogenation reaction by passing a side stream of the solvent-product-salt slurry from the reaction vessel through a filter and returning the solvent-product filtrate to the reaction vessel. This technique is particularly advantageous when the dehydrohalogenation reaction is conducted in the presence of solvent in the lower range.

For some uses, such as in coatings, adhesives and the like, it would be desirable to prepare water-soluble glycidyl ethers of glycerine having higher molecular weights since such higher molecular weight resins tend to produce coatings which exhibit greater toughness, flexibility and adhesion to substrate materials than coatings prepared from corresponding resins which are lower in molecular weight.

Such higher molecular weight water-soluble glycidyl ethers of glycerine are prepared by the process of this invention by replacing a portion of the epoxyalkyl halide with a previously prepared glycidyl ether of glycerine (hereinafter referred to as "glycidyl ether of glycerine additive"). Such glycidyl ether of glycerine additive reacts in the same manner as the epoxyalkyl halide but adds to the product chain a higher molecular weight unit.

In general, a mixture of an epoxyalkyl halide and a glycidyl ether of glycerine additive comprising from about 0.05 to about 0.65 epoxide equivalents of a glycidyl ether of glycerine additive (actually a mixture of glycidyl ethers of glycerine) and from about 1.35 to about 2.95 epoxide equivalents per mole of glycerine of an epoxyalkyl halide is added to the glycerine and the reaction conducted as hereinbefore described for the preparation of water-soluble glycidyl ethers of glycerine.

High molecular weight water-soluble glycidyl ethers of glycerine may also be prepared by replacing a portion of the epoxyalkyl halide with a diglycidyl ether of a polyoxyalkylene glycol having a molecular weight of from about 200 to about 600 in proportions of from about 0.05 to about 0.65 epoxide equivalents of the diglycidyl polyoxyalkylene glycol and from about 1.35 to about 2.95 epoxide equivalents per mole of glycerine of an epoxy alkyl halide and conducting the reaction as above described when employing the glycidyl ether of glycerine additive. Suitable diglycidyl ethers of polyoxyalkylene glycols include the diglycidyl ethers of polyoxylpropylene glycols, diglycidyl ethers of polyoxyethylene glycols and the like.

The glycidyl ether of glycerine additive and diglycidyl ether of a polyoxyalkylene glycol as previously described which may be employed in the preparation of higher molecular weight water-soluble glycidyl ethers of glycerine include any of the water-soluble glycidyl ethers of glycerine as hereinbefore described and those glycidyl ethers of glycerine and diglycidyl ethers of a polyoxyalkylene glycol having a water-insolubility as determined by the procedure hereinbefore described of less than about 67 percent and preferably less than about 10 percent.

The combined epoxide equivalents of the mixture of an epoxyalkyl halide and the glycidyl ether of glycerine additive or the diglycidyl ether of a polyoxyalkylene glycol employed is preferably from about 2.0 to about 3.0 epoxide equivalents per mole of glycerine. When the combined epoxide equivalent weights exceed about 3.0, the higher molecular weight glycidyl ethers of glycerine product obtained contains water insoluble constituents which exceed about 2 percent by volume and when the combined epoxide equivalent weights are less than about 2.0, the product tends to have relatively high proportions of monofunctional constituents.

If still higher molecular weight water-soluble glycidyl ethers of glycerine are desired, the glycidyl ether of glycerine additive may be one which was previously prepared by reacting glycerine with a mixture of an epoxyalkyl halide and a glycidyl ether of glycerine additive.

Another method of preparing high molecular weight water-soluble glycidyl ethers of glycerine is to employ as the starting material in the place of glycerine, a mixture containing (A) from about 10% to about 75%, preferably 10-49%, by weight of a polyhydroxyl-containing compound and (B) from about 90% to about 25%, preferably 90% to about 51% by weight of glycerine. When such a mixture is employed, the other components employed are based upon the combined number of moles of the individual components of the mixture, e.g. the number of moles of epoxyalkyl halide employed would be from about 2.0 to about 3.0 moles of epoxyalkyl halide per the combined number of moles of glycerine and the polyhydroxyl-containing compound.

Suitable polyhydroxyl-containing compounds include polyoxyalkylene glycols, polyglycerols and the like.

Suitable polyoxyalkylene glycols which may be employed are the polyoxyalkylene glycols wherein the alkylene portion contains from about 2 to about 4 carbon atoms and includes, for example, polyoxyethylene glycols, polyoxypropylene glycols and polyoxybutylene glycols, such glycols being represented by the formula

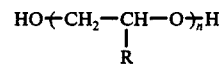

wherein R is hydrogen, methyl or ethyl and $n$ is a number such that the molecular weight of the polyoxyalkylene glycol is from about 200 to about 600.

It is also within the scope of the present invention to prepare water soluble glycidyl ethers which are the dehydrohalogenated reaction products of a mixture comprising glycerine and a polyhydroxyl-containing compound, as previously described, with a mixture comprising an epihalohydrin and a diglycidyl ether of a polyoxyalkylene glycol as previously described, a glycidyl ether of glycerine additive as previously described, or mixtures thereof.

The following specific and comparative examples are provided to more fully illustrate the invention but are not to be construed as limiting to the scope of such invention.

EXAMPLE 1

A reaction vessel was employed which was fitted with a temperature indicator, a stirrer and a condenser attached to a separating device for the aqueous and organic layers. Into such flask was added 184.2 gm. glycerine, 736 gm. ethylene dichloride and 8.52 gm. BF$_3$ etherate. After heating such mixture to 55°–60° C., epichlorohydrin was added over a period of between about 15 minutes and 6 hours while maintaining the 55°–60° C. temperature. After the epichlorohydrin addition was complete, the solution was digested at 60° C. for 30 minutes aftr which the temperature was increased to 83° C–86° C. and a quantity of 50 weight percent aqueous NaOH was slowly added thereto over a period of from 30 minutes to 8 hours while maintaining the temperature. During the NaOH addition, water was continuously removed from the reaction vessel as an azeotrope with EDC. The water was separated from the condensed azeotrope and the solvent returned to the reaction vessel. Heating and distillation continued for about 15 minutes until no more water distilled from the reaction mixture. The reaction mixture was then allowed to cool, the salt was removed by filtration, and the product was recovered by flashing the EDC solvent therefrom.

Analysis of the product was then made for percent epoxide, percent hydrolyzable chloride, percent OH and percent total chloride by standard analytical methods and percent insolubles was determined by mixing 10 gm. (9 ml) of product with sufficient water to produce a total volume of 100 ml, shaking the mixture for about 1 minute and centrifuging to remove the water-insolubles therefrom. The volume of such insolubles was then calculated as a percent by volume of the original sample.

The following table of experiments illustrates the effect of organic chloride concentration on water solubility:

distribution of the polymers as determined by gel permeation chromatography and the water-solubility of such products. The results are likewise plotted and shown graphically in FIG. 2.

The distribution of various species within the product mixture is determined by gel permeation chromatography (GPC) and therefore, referring to the product formula defined herein, the last product component GPC peak represents a product wherein the sum of $a$, $b$ and $c$ equals 0, the next to last product component peak represents a product component wherein the sum of $a$, $b$ and $c$ equals 1, the third to last such peak represents a product component wherein the sum of $a$, $b$ and $c$ equals 2, and so forth. Usually, however, the first peak or two which represent higher molecular weight material (i.e. $a + b + c =$ greater than 2) are very small peaks representing very small amounts of such higher molecular weight components. Analyses of the samples shown in Table II by vapor phase chromatography showed such samples to contain no free glycerine and therefore the product as analyzed by GPC contains only species which fall within the product definition.

Since the samples analyzed by GPC in this example are prepared from the same reactants and are therefore structurally similar, the relation of peak height to area is

TABLE I

| Experiment Number | Epi/Glycerine Mole Ratio | Caustic % of Theoretical (1) | % Insolubles | % Epoxide | % Hydrolyzable Chloride | % Total Chloride | % Organic Chloride | % Total OH |
|---|---|---|---|---|---|---|---|---|
| 1 | 2.0/1 | 87.5 | 0.0 | 30.9 | 0.0 | 1.9* | 1.9 | 8.4* |
| 2 | 2.3/1 | 72.5 | 0.0 | 28.4 | 2.89 | 5.2* | 2.31 | 8.4* |
| 3 | 2.25/1 | 75.0 | 0.0 | 28.7 | 1.78 | 6.9* | 5.12 | 8.7* |
| 4 | 2.6/1 | 87.5 | 0.0 | 32.2 | 0.0439 | 7.1* | 7.0561 | 5.3* |
| 5 | 2.6/1 | 85.0 | 0.1 | 30.3 | 0.0495 | 8.1* | 8.0505 | 4.8* |
| 6 | 3.0/1 | 85.0 | 4.45 | 31.8 | 0.025 | 9.7* | 8.675 | 4.1* |
| 7 | 3.0/1 | 70.0 | 5.67 | 30.0 | 1.94 | 11.4* | 9.46 | 5.1* |
| 8 | 3.0/1 | 85.0 | 7.8 | 31.8 | 0.028 | 9.5* | 9.472 | 3.8* |
| 9 | 3.0/1 | 66.0 | 8.9 | 26.6 | 3.25 | 12.3* | 9.05 | 5.9* |

*Analysis run by infrared - other determinations were by standard wet method.
(1) Theory caustic is calculated as an equivalent of caustic per equivalent of epichlorohydrin added to the glycerine.

FIG. 1 graphically demonstrates the effect of organic chloride concentration in the final resin. This figure was obtained by plotting % total organic chloride (% total chloride - % hydrolyzable chloride) against the % insolubles of the final product of the experiments shown in Table I.

substantially constant. Therefore, for purposes of this Example the percent of products falling within a given peak or peaks is determined by dividing the height of such peak (or sum of heights of two or more peaks) by the sum of all the peak heights time 100.

TABLE II

| Experiment No. | Epi/Glycerine Mole Ratio | Caustic % of Theoretical (1) | % Insolubles | % Epoxide | % Hydrolyzable Chloride | % Total Chloride | % Organic Chloride | % Total OH | Peak Height in mm | | | | % of Product Having $a+b+c=>1$ |
|---|---|---|---|---|---|---|---|---|---|---|---|---|---|
| | | | | | | | | | Last Peak (a+b+c=0) | Third Peak (a+b+c=1) | Second Peak (a+b+c=2) | First Peak (a+b+c=>2) | |
| 1 | 2.25/1 | 87.5 | 0.0 | 32.8 | 0.008 | 7.1 | 7.092 | 7.3 | 130 | 115 | 51 | 26 | 23.9 |
| 2 | 2.5/1 | 85.0 | 0.0 | 30.2 | 0.184 | 6.6 | 6.416 | 7.0 | 113 | 123 | 59 | 33 | 28.0 |
| 3 | 2.5/1 | 87.5 | 0.0 | 32.4 | 0.0035 | 7.9 | 7.8965 | 6.0 | 122 | 128 | 66 | 34 | 28.6 |
| 4 | 2.5/1 | 85.0 | 0.0 | 30.4 | 0.145 | 8.1 | 7.955 | 7.4 | 110 | 125 | 65 | 34 | 29.6 |
| 5 | 2.3/1 | 72.5 | 0.0 | 28.4 | 2.89 | 5.2* | 2.31 | 8.4 | 106 | 105 | 69 | 38 | 33.6 |
| 6 | 2.6/1 | 85.0 | 0.10 | 30.3 | 0.0495 | 8.1* | 8.0505 | 4.8* | 85 | 105 | 60 | 34 | 33.1 |
| 7 | 2.5/1 | 85.0 | 0.78 | 30.9 | 0.14 | 9.0 | 8.86 | 2.3 | 92 | 145 | 84 | 38 | 33.9 |
| 8 | 3.0/1 | 85.0 | 7.8 | 31.8 | 0.028 | 9.5* | 9.472 | 3.8* | 85 | 116 | 78 | 42 | 37.4 |

*Analysis run by infrared - other determinations were by standard wet method.
(1) Theory caustic is calculated as an equivalent of caustic per equivalent of epichlorohydrin added to the glycerine.

in Table I.

EXAMPLE 2

In the same manner as Example 1, glycidyl ethers of glycerine were prepared having various molecular weight distributions to demonstrate the effect of various proportions of various molecular species within the polymer on water-solubility. The following Table II shows the specific reaction condition, the molecular

EXAMPLE 3

In the same manner as Example 1, a number of experiments were conducted and tabulated to show the effects of solvent type and concentration, catalyst, and mole ratio of reactants as well as to provide a direct comparison with the water-solubility of a typical commercial glycidyl ether of glycerine. The indicated catalyst was employed in a quantity corresponding to 0.01 equivalent of catalyst per glycerine OH equivalent. The results of such experiments are shown in the following Table III.

conducted to show the preparation of higher molecular weight water-soluble glycidyl ethers of glycerine and to show the effect of variations in the combined epoxide equivalent weight of the epoxy alkyl halide and the glycidyl ether of glycerine additive. The results of such

TABLE III

| | Epichlorohydrin - Glycerine Reaction | | | Dehydrohalogenation | | | | | | | |
|---|---|---|---|---|---|---|---|---|---|---|---|
| Experiment No. | Epi-Glycerine Mole Ratio | Solvent-Wt.% Based on Glycerine | Catalyst | Solvent Wt. % Based on Glycerine | Caustic % of Theoretical (1) | Insolubles % | Epoxide % | Hydrolyzable Chloride % | Total Chloride % | Organic Chloride % | Total OH % |
| 1 (Control) A typical, commercially available glycidyl ether of glycerine having an eq. wt. of 150 – 170. | | | | | | 23.3 | 26.0 | 1.03 | 13.8 | 11.17 | 4.2 |
| 2** | 2.5/1 | none | $BF_3$ | Toluene 90% | 85.0 | 11.1 | 30.5 | 0.16 | 11.4 | 11.24 | 3.9 |
| 3 | 2.5/1 | EDC-80% | $BF_3$ | EDC-80% | 85.0 | 0.00 | 30.2 | 0.184 | 6.6 | 6.42 | 7.0 |
| 4 | 2.5/1 | None | $SnCl_4$ | EDC-80% | 85.0 | 1.1 | 30.5 | 0.592 | 5.6 | 5.01 | 4.3 |
| 5 | 2.6/1 | EDC-80% | $BF_3$ | EDC-80% | 87.5 | 0.0 | 32.2 | 0.044 | 7.1* | 7.05 | 5.3* |
| 6 | 3.0/1 | EDC-80% | $BF_3$ | EDC-80% | 70.0 | 5.67 | 30.0 | 1.94 | 11.4* | 9.46 | 5.1* |
| 7 | 2.3/1 | EDC-80% | $BF_3$ | EDC-80% | 72.5 | 0.0 | 28.4 | 2.89 | 5.2 | 2.31 | 8.4 |
| 8 | 3.0/1 | EDC-80% | $BF_3$ | EDC-80% | 85.0 | 4.45 | 31.8 | 0.025 | 9.7* | 9.68 | 4.1* |
| 9 | 3.0/1 | EDC-80% | $BF_3$ | EDC-80% | 85.0 | 5.57 | 31.8 | 0.064 | 7.1* | 7.04 | 5.0* |
| 10 | 2.5/1 | EDC-80% | $BF_3$ | EDC-80% | 85.0 | 0.00 | 31.4 | 0.13 | | | |
| 11 | 3.0/1 | EDC-80% | HF (50% aq. sol.) | EDC-80% | 85.0 | 0.22 | 33.0 | 0.073 | 8.32 | 8.82 | 6.7 |

*Analyses run by Infrared - other determinations were by Standard Wet Method.
**Dehydrohalogenation reaction conducted at 30° C and 35 – 40 mm Hg instead of 83° – 86° C at 760 mm Hg.
(1) Theoretical amount of caustic is calculated as an equivalent of caustic per equivalent of epichlorohydrin added to the glycerine.

EXAMPLE 4

In the same manner as Example 1, experiments were experiments are summarized in the following Table IV:

TABLE IV

| Experiment No. | Additive Employed as a Mixture with Epichlorohydrin | Insolubles in Additive, Vol. % | Equivalents of Additive/2 moles of Glycerine | Equivalents of Epichlorohydrin/ 2 moles of Glycerine | Equivalents of Additive + Epichlorohydrin/ 1 mole Glycerine | Caustic, % of Theoretical (1) | Insolubles in Product, Vol. % | % Epoxide | % Hydrolyzable Chloride | % Total Chloride | % Total OH |
|---|---|---|---|---|---|---|---|---|---|---|---|
| 1  | Expt. 3 of Ex. 1   | 0.0  | 0.288 | 3.712 | 2.0   | 90.0 | 0.0  | 26.8 | 0.04   | <1.0*  | 8.6* |
| 2  | Expt. 1 of Ex. 1   | 0.0  | 0.144 | 3.856 | 2.0   | 85.0 | 0.5  | 29.2 | 0.086  | 1.0*   | 8.5* |
| 3  | Expt. 1 of Ex. 1   | 0.0  | 0.420 | 3.580 | 2.0   | 87.5 | 0.0  | 25.9 | 0.172  | <1.0*  | 9.9* |
| 4  | Expt. 6 of Ex. 2   | 0.1  | 0.144 | 5.056 | 2.6   | 87.5 | 0.0  | 29.9 | 0.0413 | 7.0*   | 5.5* |
| 5  | Expt. 8 of Ex. 3   | 4.45 | 0.300 | 5.200 | 2.75  | 72.5 | 3.33 | 27.0 | 2.10   | 8.7*   | 8.1* |
| 6  | Expt. 9 of Ex. 3   | 5.57 | 0.416 | 5.584 | 3.00  | 85.0 | 7.78 | 28.2 | 0.051  | 7.1*   | 5.0* |
| 7  | Expt. 6 of Ex. 1   | 4.45 | 0.200 | 5.000 | 2.6   | 72.5 | 1.11 | 26.0 | 2.20   | 9.0*   | 8.4* |
| 8  | Expt. 10 of Ex. 3  | 0.00 | 0.144 | 5.056 | 2.6   | 72.5 | 0.22 | 26.4 | 2.48   | 8.9*   | 8.3* |
| 9  | Expt. 8 of Ex. 4   | 0.22 | 0.191 | 5.009 | 2.6   | 72.5 | 0.89 | 26.5 | 1.80   | 9.0*   | 8.2* |
| 10 | Expt. 10 of Ex. 3  | 0.00 | 0.245 | 4.955 | 2.6   | 87.5 | 1.11 | 28.9 | 0.18   | 8.5*   | 4.7* |
| 11 | Expt. 3 of Ex. 3   | 0.0  | 0.338 | 4.862 | 2.6   | 87.5 | 0.0  | 27.4 | 0.043  | 7.5    | 7.7  |
| 12 | Expt. 3 of Ex. 3   | 0.0  | 0.576 | 4.624 | 2.6   | 87.5 | 0.0  | 24.7 | 0.075  | 6.6    | 8.4  |
| 13 | Expt. 3 of Ex. 3   | 0.0  | 1.08  | 4.12  | 2.6   | 90.0 | 0.0  | 19.6 | 0.024  | 5.7    | 9.2  |
| 14 | Expt. 3 of Ex. 3   | 0.0  | 1.08  | 3.12  | 2.1   | 90.0 | 0.0  | 16.7 | 0.16   | 5.6    | 13.2 |
| 15 | DER 732**          | 66.7 | 0.078 | 2.52  | 1.294 | 87.5 | 0.8  | 27.7 | 0.064  | 7.4    | 5.6  |

*Analysis run by infrared - other determinations by standard wet method.
**DER 732 is the diglycidyl ether of a 400 molecular weight polyoxyalkylene glycol, said diglycidyl ether having an epoxide equivalent weight of 330.
(1) Theoretical amount of caustic is calculated as an equivalent of caustic per equivalent of epichlorohydrin added to the glycerine.

EXAMPLE 5

A reaction vessel was employed which was fitted with a temperature indicator, a stirrer, a condenser attached to a separating device for aqueous and organic layers and a means for continuously removing a slurry of reactants, products and salt, separating the salt from said slurry and returning the liquid portion thereof to the reaction vessel. Into such a vessel was charged 92.1 grams (1 mole) of glycerine, 138.0 grams of ethylene dichloride and 4.25 grams (0.03 moles) of boron trifluoride etherate. The temperature of the reaction vessel contents was raised to 55°–60° C and 229.0 grams (2.477 moles) of epichlorohydrin containing 17.5 grams (0.122 epoxide equivalents) of the product from experiment 2 of Example 2 was added over a period of 1 hour. The temperature was allowed to exotherm to 90° C (reflux) during the addition. After digesting for 15 minutes at 90° C, 78.2 grams (1.98 moles) of 50% aqueous sodium hydroxide was slowly added at 88° C. As the caustic was added, the water was continuously removed as an ethylene dichloride-water azeotrope and the ethylene dichloride was returned to the vessel. Also as the caustic was added, a salt slurry from the reaction vessel was continuously circulated through a filter to remove the salt and the liquid portion thereof was returned to the reaction vessel. After all the caustic had been added, the reaction was continued until no more water was collected. The ethylene dichloride containing the product was then pumped out of the reaction vessel through the filter and the ethylene dichloride solvent was removed from the product by distilling under reduced pressure. The % yield of recovered product was 90.2. The product had the following properties.

| % epoxide | 27.06 |
|---|---|
| % insolubles | 0.0 |
| % total chloride | 6.76 |
| % total OH | 6.76 |
| % hydrolyzable chloride | 0.02 |

EXAMPLE 6

A reaction vessel was employed which was fitted with a temperature indicator, a stirrer and a condenser attached to a separating device for aqueous and organic layers. Into such a vessel was charged 92.1 grams (1 mole) of glycerine, 23 grams of ethylene dichloride and 4.25 grams of boron trifluoride etherate. The temperature of reaction vessel contents was raised to 55°–60° C and 229.0 grams (2.477 moles) of epichlorohydrin containing 17.5 grams (0.122 epoxide equivalents) of the product from experiment 2 of example 2 was added over a period of 1 hour. The temperature was allowed to exotherm to 90° C (reflux) during the addition. After digesting for 30 minutes at 90° C, the contents were cooled to 84° C and 345 grams of ethylene dichloride were added. The temperature was maintained at 84° C and 173.5 grams (2.16 moles) of 50% aqueous sodium hydroxide was slowly added over a 2-hour period. As the NaOH was added, water, produced by the reaction and introduced with the NaOH, was continuously removed as an ethylene dichloride-water azeotrope and the ethylene dichloride was separated from the water and returned to the reaction vessel via the separating device. Ater all the water added with the caustic and that produced by the epoxidation reaction had been removed, the contents were digested for 15 minutes at 83° C. The salt was then removed from the product-ethylene dichloride-salt slurry by filtration and the product recovered from the product-ethylene dichloride filtrate by removing the ethylene-dichloride by distillation under reduced pressure. A 93.6% yield of product was recovered, such product having the following properties:

| % epoxide | 27.3 |
|---|---|
| % insolubles | 1.95 |
| % hydrolyzable chloride | 0.35 |
| % total chloride | 8.03 |
| % total OH | 6.59 |

EXAMPLE 7

A reaction vessel was employed which was fitted with a temperature indicator, a stirrer and a condenser attached to a separating device for the aqueous and organic layers. Into such flask was added glycerine and polyhydroxyl containing compounds, ethylene dichloride (75 wt. percent based on solvent, glycerol and polyhydroxyl-containing compounds), and $BF_3$ etherate (0.03 mole per total moles of glycerine and polyhydroxyl-containing compound). After heating such mixture to 55°–60° C., epichlorohydrin was added over a period of between about 15 minutes and 6 hours while maintaining the 55°–60° C. temperature. After the epichlorohydrin addition was complete, the solution was digested at 60° C. for 30 minutes after which the temperature was increased to 83°–86° C. and a quantity of 50 weight percent aqueous NaOH was slowly added thereto over a period of from 30 minutes to 8 hours while maintaining the temperature. During the NaOH addition, water was continuously removed from the reaction vessel as an azeotrope with EDC. The water was separated from the condensed azeotrope and the solvent returned to the reaction vessel. Heating and distillation continued for about 15 minutes until no more water distilled from the reaction mixture. The reaction mixture was then allowed to cool, the salt was removed by filtration, and the product was recovered by flashing the EDC solvent therefrom.

Analysis of the product was then made for percent epoxide, percent hydrolyzable chloride, percent OH and percent total chloride by standard analytical methods and percent insolubles was determined by mixing 10 gm. (9 ml) of product with sufficient water to produce a total volume of 100 ml, shaking the mixture for about 1 minute and centrifuging to remove the water-insolubles therefrom. The volume of such insolubles was then calculated as a percent by volume of the original sample.

The following table of experiments (Table V) gives the results obtained from each experiment.

TABLE V

| Experiment No. | Compound Mixed with Glycerine Type | Quantity (wt.% based on total wt. of glycerine + compound) | Moles of Epichlorohydrin/ total moles of glycerine + compound mixed with glycerine | Caustic % of Theoretical (1) | % Insolubles | % Hydrolyzable Chloride | % Total Chloride | % OH | % Epoxide |
|---|---|---|---|---|---|---|---|---|---|
| 1 | polyglycerol mw = 388 | 20 | 2.6 | 87.5 | 0.0 | <0.005 | 7.66 | 5.9 | 29.0 |
| 2 | " | 30 | 2.6 | 87.5 | 0.0 | 0.026 | 8.4 | 6.4 | 28.0 |
| 3 | " | 50 | 2.6 | 87.5 | 0.0 | 0.022 | 6.6 | 10.9 | 24.0 |
| 4 | " | 50 | 2.0 | 87.5 | 0.0 | 0.032 | 6.9 | 18.2 | 19.8 |
| 5 | " | 70 | 2.0 | 87.5 | 2.2 | 0.05 | 9.2 | 18.3 | 14.8 |
| 6 | polyoxypropylene glycol, mw = 400 | 33.1 | 1.6 | 90.0 | 0.0 | 0.03 | 3.5 | 11.6 | 22.6 |
| 7 | " | 56.8 | 1.6 | 90.0 | 0.0 | 0.024 | 2.46 | 9.86 | 17.8 |

We claim:

1. A process for the preparation of a water-soluble mixture of glycidyl ethers of glycerine wherein
   (A) glycerine is reacted in a vessel with from about 2.0 to about 2.6 moles of epichlorohydrin per mole of glycerine in the presence of a catalyzing amount of a Lewis Acid catalyst wherein the reaction is conducted in an organic solvent in which the glycerine is at least partially soluble and in which the chlorohydrin ether reaction product will form a single phase, said solvent being present in a quantity of from about 20% to about 90% by weight of the quantity of glycerine employed, the reaction being conducted at a temperature of from 0° C to the reflux temperature of the solvent phase;
   (B) dehydrohalogenating, at a temperature below about 110° C, the chlorohydrin ether reaction product with from about 70 to about 95% of the theoretical amount of NaOH in the presence of ethylene dichloride in a quantity of 50–95% by weight based upon the initial weight of glycerine employed plus the total quantity of solvent employed in this dehydrohalogenation step;
   (C) separating the water resulting from the dehydrohalogenation reaction and caustic addition by azeotropic distillation, and
   (D) separating the salt from the resulting solution; with the proviso that when the solvents employed in steps (A) and (B) are different, the solvent in (A) is removed before performing step (B); wherein said mixture of glycidyl ethers of glycerine contains less than 2% by volume of insolubles as determined by placing 9 ml of the resin in water to a total volume of 100 ml, agitating until no more resin is apparently going into solution, thereafter centrifuging to remove the insolubles and calculating the percent insolubles by the following equation:

$$\frac{\text{milliliters of insolubles}}{9} \times 100 = \% \text{ insolubles by volume}$$

and wherein said mixture contains from about 1.5 to about 8% organic chloride and an epoxide content of from about 28.4% to about 33% by weight.

2. The process of claim 1 wherein the organic solvent in step (A) is ethylene dichloride.